(12) United States Patent
Boser

(10) Patent No.: US 8,862,245 B2
(45) Date of Patent: Oct. 14, 2014

(54) ELECTRODE CONSTRUCTION FOR IMPLANTABLE MEDICAL ELECTRICAL LEADS

(71) Applicant: Medtronic, Inc., Minneapolis, MN (US)

(72) Inventor: Gregory A Boser, Richfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 126 days.

(21) Appl. No.: 13/664,782

(22) Filed: Oct. 31, 2012

(65) Prior Publication Data

US 2014/0121736 A1    May 1, 2014

(51) Int. Cl.
*A61N 1/05*    (2006.01)

(52) U.S. Cl.
USPC .............................. 607/121; 607/116; 607/119

(58) Field of Classification Search
None
See application file for complete search history.

(56) References Cited

U.S. PATENT DOCUMENTS

| | | | |
|---|---|---|---|
| 4,440,178 A * | 4/1984 | Bussard et al. ............... | 607/121 |
| 4,674,009 A | 6/1987 | Wong | |
| 5,849,031 A * | 12/1998 | Martinez et al. ............... | 607/121 |
| 6,501,992 B1 | 12/2002 | Belden et al. | |
| 7,047,082 B1 * | 5/2006 | Schrom et al. ................ | 607/116 |
| 7,612,291 B2 | 11/2009 | Chastain et al. | |
| 7,887,681 B2 * | 2/2011 | Zhou ............................. | 204/292 |
| 2004/0064175 A1 | 4/2004 | Lessar et al. | |
| 2006/0193889 A1 * | 8/2006 | Spradlin et al. ............... | 424/423 |
| 2006/0282126 A1 | 12/2006 | Fischbach et al. | |
| 2007/0038278 A1 | 2/2007 | Zarembo | |
| 2007/0265692 A1 * | 11/2007 | Koop et al. .................... | 607/119 |
| 2008/0161886 A1 | 7/2008 | Stevenson et al. | |
| 2010/0010560 A1 | 1/2010 | Taylor et al. | |
| 2010/0211147 A1 * | 8/2010 | Schiefer et al. ............... | 607/116 |

OTHER PUBLICATIONS

C00001139.WOU2 (PCT/US2013/064824) PCT Notification of Transmittal of the International Search Report and the Written Opinion of the International Searching Authority.
"There's only one thing tantalum can't do: Give up.", Sep. 26, 2012, 14 pp, www.plansee.com.

* cited by examiner

*Primary Examiner* — Kennedy Schaetzle
(74) *Attorney, Agent, or Firm* — Michael C. Soldner

(57) ABSTRACT

An implantable electrode for electrical stimulation of a body, for example, being a component of an implantable medical electrical lead, is preferably in the form of a coiled conductor wire, wherein the wire is formed by a tantalum (Ta) core directly overlaid with a platinum-iridium (Pt—Ir) cladding. When a maximum thickness of the Pt—Ir cladding defines a cladded zone between an outer, exposed surface of the electrode and the Ta core, a surface of the Ta core encroaches into the cladded zone by no more than approximately 50 micro-inches. The tantalum core may be cold worked to improve surface quality or formed from a sintered and, preferably, grain stabilized tantalum.

14 Claims, 4 Drawing Sheets

ELECTRODE CONSTRUCTION FOR IMPLANTABLE MEDICAL ELECTRICAL LEADS

FIELD OF THE DISCLOSURE

The present invention pertains to implantable medical electrical leads, and more particularly to electrode constructions thereof.

BACKGROUND

Implantable medical systems that are designed to deliver electrical stimulation, for example, to cardiac muscle or the spinal cord, and/or to monitor bodily electrical activity, typically include a relatively compact implantable device to which one or more elongate implantable electrical leads are coupled, for example, like the exemplary system 10 schematically shown in FIG. 1A. FIG. 1A illustrates system 10 including an implantable defibrillator device 500 and a defibrillation lead 100, which is connected to device 500 and extends transvenously therefrom, into a heart of a patient, such that a defibrillation electrode 11 and a pace-sense electrode 13 of lead 100 are located in the right ventricle of the heart. Those skilled in the art appreciate that a power source and circuitry of device 500 are contained in a hermetically sealed housing 55 of device 500, which housing 55, being formed from a conductive metal such as titanium, may function as an electrode, in concert with electrode 11, to deliver high voltage pulses for defibrillation therapy in response to a cardiac arrhythmia, for example, sensed by electrodes 13, 11.

With reference to FIG. 1B, an outer insulation sheath 12 of lead 100 contains a first elongate conductor 20 that couples electrode 11 to a contact 151 of a connector terminal 15 of lead 100, and a second elongate conductor 135, which is isolated from first conductor 20 and couples electrode 13 to a contact pin 153 of terminal 15. FIG. 1A further illustrates device 500 including a connector module 51 that has a port 501 into which connector terminal 15 is inserted for electrical coupling with the circuitry contained in housing 55, for example, via electrical contacts, which are mounted within port 501 and coupled to the circuitry via hermetically sealed feedthroughs. Suitable constructions for such a connector module and lead connector are known to those skilled in the art.

With further reference to FIGS. 1A-B, electrode 11 is shown formed by a coiled conductor wire, which may be an exposed distal portion of conductor 20 or a separately formed coil coupled to conductor 20, for example, by a weld or a crimp joint. Those skilled in the art typically construct stimulation and sensing electrodes, like electrode 11, from a platinum-iridium alloy (Pt—Ir), since Pt—Ir provides an effective bio-stable, bio-compatible, and corrosion-resistant electrode surface interface.

SUMMARY

Embodiments of the present invention pertain to electrode constructions in which a tantalum (Ta) core is overlaid with a Pt—Ir cladding. Embodiments of electrodes are preferably in the form of a coiled conductor wire, wherein the wire includes a Ta core and a Pt—Ir cladding directly overlaying the core and forming an exposed outer surface of the electrode. A cladded zone, between the exposed outer surface and the Ta core, may be defined by a maximum thickness of the Pt—Ir cladding, and, according to some embodiments of the present invention, the surface of the Ta core encroaches into this cladded zone by no more than approximately 50 micro-inches (0.00005 inch). The surface of the Ta core may be modified, to improve a surface quality thereof, by a cold working process, such as peening or swaging, prior a drawing process that forms the Pt—Ir cladded wire. According to alternate embodiments, the Ta core is formed from a sintered, and, preferably, grain-stabilized Ta having the desired surface quality without the need for the aforementioned cold working. A nominal thickness of the Pt—Ir cladding, according to some embodiments, is between approximately 100 micro-inches (0.0001 inch) and approximately 500 micro-inches (0.0005 inch), for example, when an outer diameter of the cladding is between approximately 0.005 inch and approximately 0.007 inch.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1A:
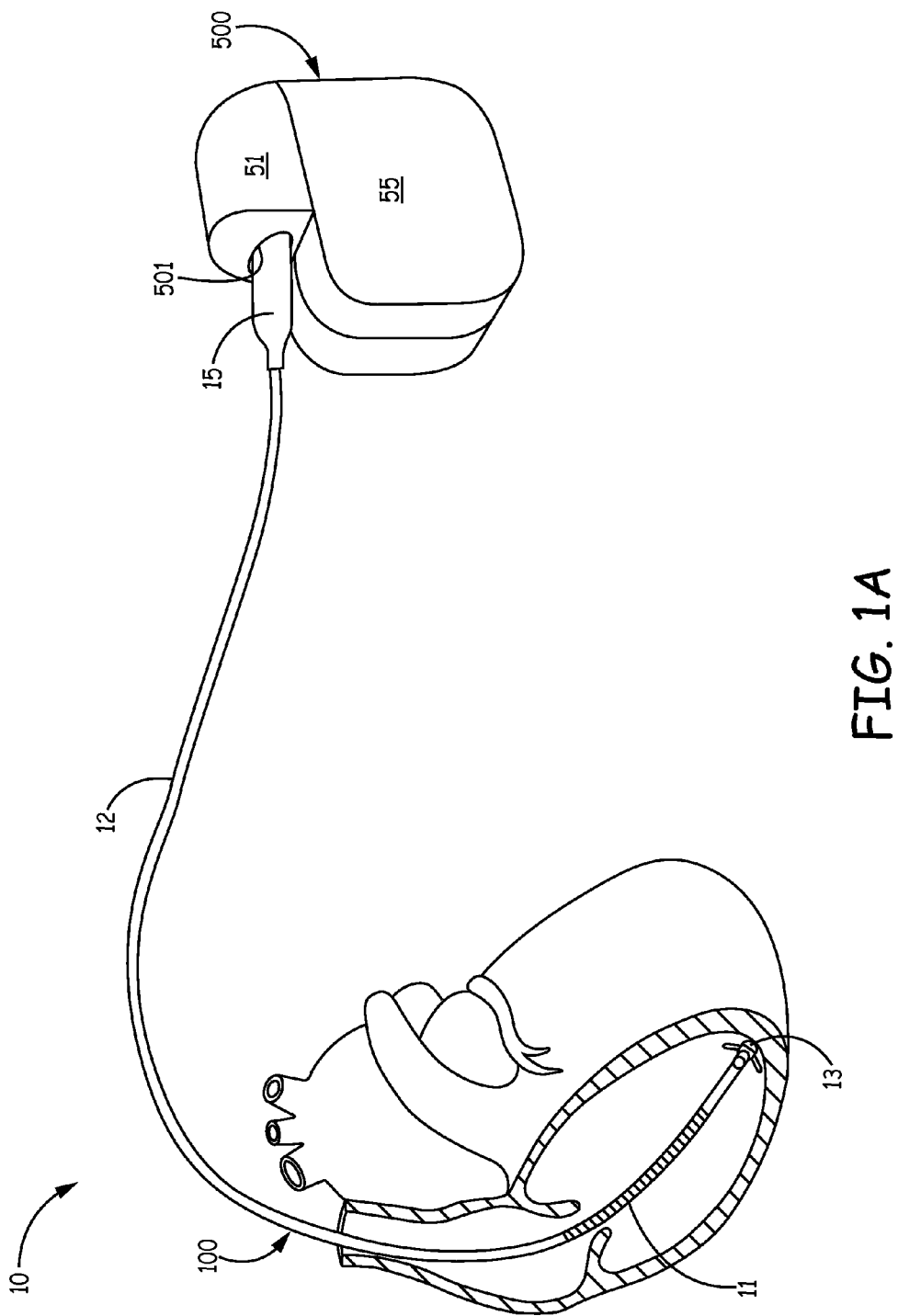
FIG. 1A is a schematic depicting an exemplary implantable medical system.
Figure 1B:
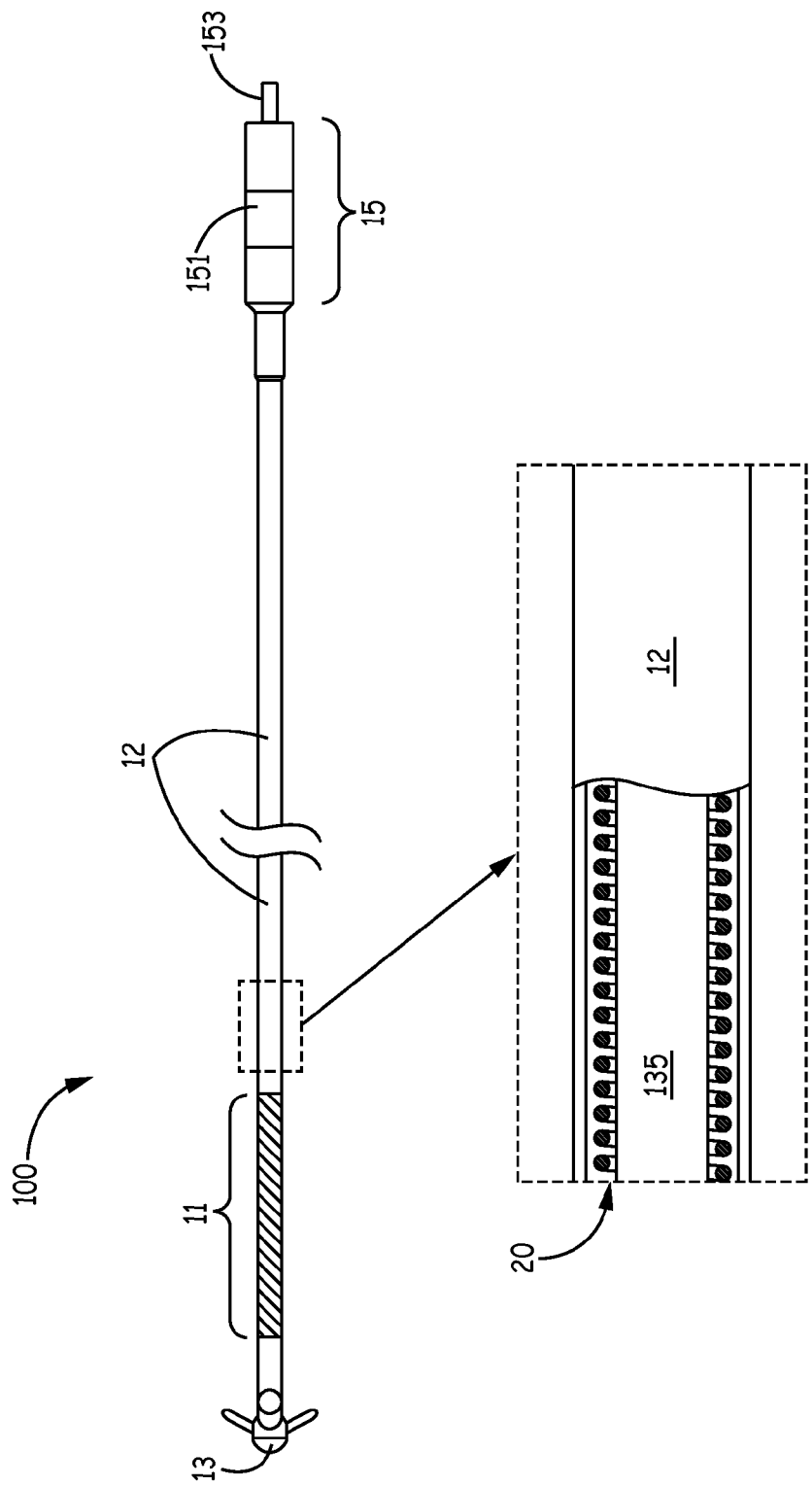
FIG. 1B is a plan view, with an enlarged cut-away cross-section, of an implantable medical electrical lead, which may include an electrode constructed according to some embodiments of the present invention.

FIG. 1B is a plan view, with an enlarged cut-away cross-section, of implantable medical electrical lead 100. Electrode 11 is preferably formed by an exposed distal portion of conductor coil 20, which extends distally out from insulation sheath 12. Alternately, electrode 11 is formed from a separate member, for example, another coiled conductor wire, which is coupled to conductor coil 20 for example, by a crimp joint and/or a weld joint, according to methods known in the art. One or more conductor wires, which are coiled to form electrode 11 have an exposed outer surface formed by a Pt—Ir cladding that overlays a Ta core. This composite type wire is formed as a drawn-filled-tube (DFT®) by a cold-drawn process known to those skilled in the art.

Figure 2B:
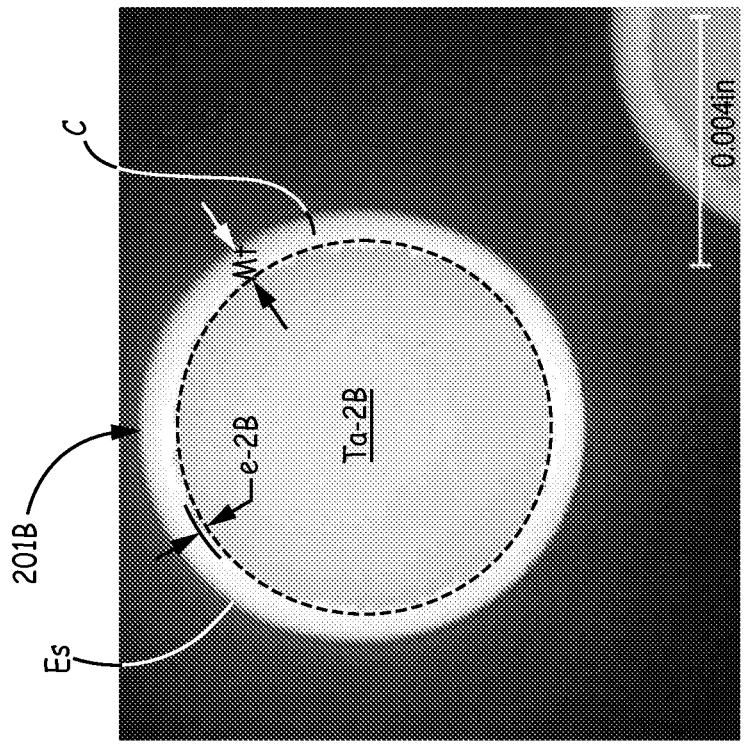
FIGS. 2B-C are cross-section views of Pt—Ir cladded conductor wires having improved cores, according to some embodiments of the present invention.
Figure 2A:
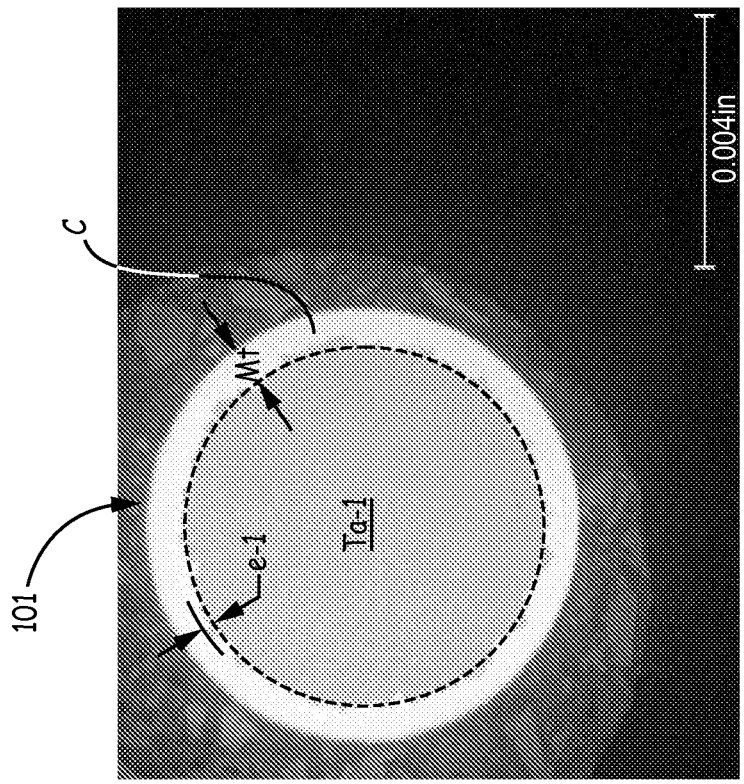
FIG. 2A is a cross-section view of a prior art Pt—Ir cladded conductor wire.
Figure 2C:
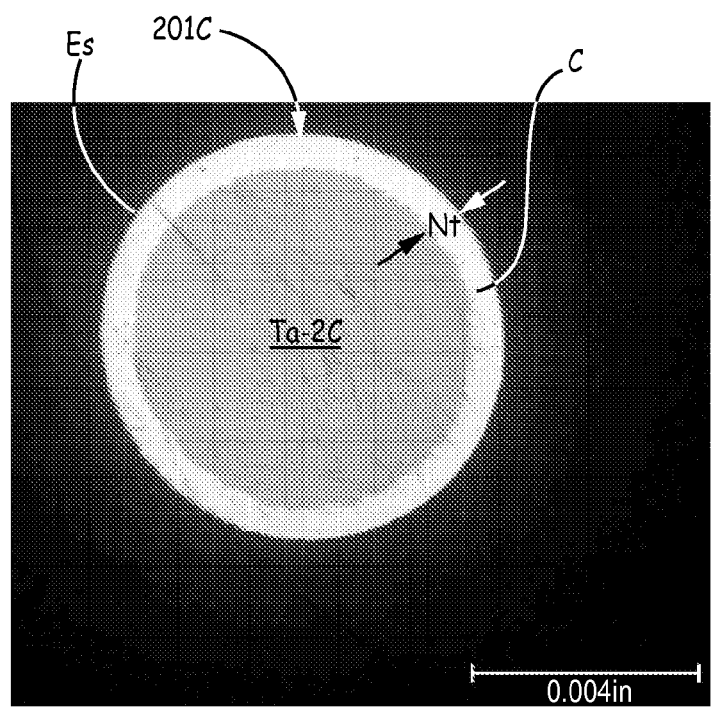

FIG. 2A is a cross-section view (micrograph) of a prior art conductor wire 101, which includes a Ta core Ta-1 overlaid by a Pt—Ir cladding C. FIG. 2A illustrates cladding C having a maximum thickness Mt of approximately 500 to 600 micro-inches (0.0005-0.0006 inch), which defines a cladded zone of wire 101. The inner perimeter of the cladded zone is designated with a dashed line. FIG. 2A further illustrates core Ta-1 having a surface roughness that encroaches into the cladded zone, for example, by a distance e-1, which may be as large as between approximately 200 to 300 micro-inches. Because such an encroachment of core Ta-1 causes a minimum thickness of cladding C to be significantly smaller than the maximum thickness Mt, specification of an increased nominal cladding thickness for wire 101 may be necessary to meet a minimum wall thickness requirement for cladding C. The specification of increased nominal Pt—Ir cladding thickness is contrary to a desired reduction in cladding thickness that can translate into cost savings, and may facilitate a reduction in the profile of electrodes, such as electrode 11, for example, by allowing the winding of a smaller diameter coil. FIGS. 2B-C are cross-section views (micrographs) of conductor wires 201B, 201C, each of which includes a tantalum core Ta-2B, Ta-2C, respectively, that has improved surface quality, according to some embodiments of the present invention, for example, to facilitate the desired reduction in nominal Pt—Ir cladding thickness.

The surface roughness of each of cores Ta-1, Ta-2B, Ta-2C is related to the grain structure (size, texture and orientation) of the corresponding starting material—a Ta rod assembled into Pt—Ir tubing at the start of the aforementioned DFT® drawing process. If the Ta rod is melted quality Ta, for example, vacuum-arc melted or electron-beam melted (UNS R05200), then, during the drawing process, although many of the grains are broken down to produce a finer grain structure with more uniform orientation, those grains that do not break down can end up protruding from the surface of the Ta core to encroach into the cladded zone, as illustrated in FIG. 2A. According to some embodiments, the surface quality of the Ta rod (melted quality) may be modified by cold working, for example, peening or swaging, in order to refine the starting grain size of the Ta, prior to the drawing process. But, according to some alternate embodiments, for example, as illustrated in FIGS. 2B-C, the Ta rod is formed from a sintered quality tantalum that has an inherently finer grain structure.

FIG. 2B illustrates Pt—Ir cladding C of wire 201B, having maximum thickness Mt defining a cladded zone that extends from an inner perimeter, indicated with a dashed line, to an outer exposed surface Es of the cladding C, wherein maximum thickness Mt is approximately 500 to 600 micro-inches, similar to that of wire 101 of FIG. 2A. However, an encroachment e-2B of core Ta-2B is significantly reduced from that of wire 101. According to preferred embodiments, encroachment e-2B is no greater than approximately 50 micro-inches (0.00005 inch); and, according to the illustrated embodiment, a starting material for core Ta-2B is a Ta rod of sintered quality, for example, being powder metallurgy consolidated (UNS R05400), as produced by PLANSEE SE of Austria (www.plansee.com). According to some embodiments, a coil electrode, like electrode 11 of FIGS. 1A-B, is formed from a wire, like wire 201B, wherein exposed surface Es of Pt—Ir cladding C forms an exposed surface of the coil electrode. An outer diameter of cladding C of wire 201B is approximately 0.007 inch, but may be approximately 0.005 inch, according to some alternate embodiments.

FIG. 2C illustrates wire 201C including Ta core Ta-2C having been formed from a sintered quality and grain stabilized Ta rod, such that an encroachment of the surface of core Ta-2C into the Pt—Ir cladding C of wire 201C is minimized to the point that a nominal thickness Nt of cladding C approaches the maximum thickness Mt of cladding C. The sintered and grain stabilized Ta rod, for example, designated TaKS as produced by PLANSEE SE, has an even finer grain structure than that of the Ta rod for core Ta-2B of FIG. 2B, due to silicon and/or yttrium additives (on order of 100's of ppm), which inhibit grain growth during annealing. According to some preferred embodiments, a coil electrode, like electrode 11 of FIGS. 1A-B, is formed from a wire, like wire 201C, wherein exposed surface Es of Pt—Ir cladding C forms an exposed surface of the coil electrode; and, since the surface of core Ta-2C does not significantly encroach into the cladded zone, cladding nominal thickness Nt can be reduced from the illustrated 500 to 600 micro-inches to between approximately 100 to 500 micro-inches, preferably between approximately 100 and 350 micro-inches, according to some embodiments. An outer diameter of cladding C of wire 201C is approximately 0.007 inch, but may be approximately 0.005 inch, according to some embodiments.

In the foregoing detailed description, the invention has been described with reference to specific embodiments. However, it may be appreciated that various modifications and changes can be made without departing from the scope of the invention as set forth in the appended claims.

The invention claimed is:

1. An implantable electrode for electrical stimulation of a body, the electrode comprising a platinum-iridium cladding directly overlaying a tantalum core, the cladding forming an exposed surface of the electrode and having a maximum thickness defining a cladded zone between the exposed outer surface and the core, and wherein the improvement comprises: the tantalum core having a surface that encroaches into the cladded zone by no more than approximately 50 micro-inches.

2. The electrode of claim 1, wherein a nominal thickness of the cladding is between approximately 100 micro-inches and approximately 500 micro-inches.

3. The electrode of claim 2, wherein the nominal thickness is between approximately 100 micro-inches and approximately 350 micro-inches.

4. The electrode of claim 2, wherein the cladding and the core comprise a conductor wire, and an outer diameter of the cladding is between approximately 0.005 inch and approximately 0.007 inch.

5. The electrode of claim 1, wherein the tantalum core comprises a sintered grain-stabilized tantalum.

6. The electrode of claim 1, wherein the cladding and the core comprise a conductor wire.

7. The electrode of claim 6, wherein the surface of the tantalum core is modified by a cold working process, separate from the cladding, prior to a drawing process to form the conductor wire, the cold working process comprising one of: peening and swaging.

8. An implantable electrode for electrical stimulation of a body, the electrode comprising a coiled conductor wire, and the wire comprising a sintered grain-stabilized tantalum.

9. The electrode of claim 8, wherein the conductor wire further comprises a platinum-iridium cladding directly overlaying the sintered grain-stabilized tantalum, the cladding forming an exposed surface of the electrode.

10. The electrode of claim 9, wherein a nominal thickness of the cladding is between approximately 100 micro-inches and approximately 500 micro-inches.

11. The electrode of claim 10, wherein the nominal thickness is between approximately 100 micro-inches and approximately 350 micro-inches.

12. A medical electrical lead comprising a continuous conductor wire wound in a coil, the conductor wire having an insulated length, extending distally from a connector terminal of the lead, and an electrode length, extending distally from the insulated length; and wherein the improvement comprises: the conductor wire comprising a platinum-iridium cladding overlaying a sintered grain-stabilized tantalum core.

13. The lead of claim 12, wherein a nominal thickness of the cladding of the conductor wire is between approximately 100 micro-inches and approximately 500 micro-inches.

14. The lead of claim 13, wherein the nominal thickness is between approximately 100 micro-inches and approximately 350 micro-inches.

\* \* \* \* \*